United States Patent [19]

Okashita

[11] Patent Number: 4,756,613

[45] Date of Patent: Jul. 12, 1988

[54] EYE FUNDUS CAMERA HAVING VIEWING TARGETS

[75] Inventor: Toshihiro Okashita, Tokyo, Japan

[73] Assignee: Tokyo Kogaku Kikai Kabushiki Kaisha, Tokyo, Japan

[21] Appl. No.: 117,378

[22] Filed: Oct. 28, 1987

Related U.S. Application Data

[63] Continuation of Ser. No. 016,502, Feb. 18, 1987, abandoned, which is a continuation of Ser. No. 648,650, Sep. 7, 1984, abandoned.

[30] Foreign Application Priority Data

Sep. 14, 1983 [JP] Japan .................................. 58-170388

[51] Int. Cl.⁴ .......................... A61B 3/14; G03B 29/00
[52] U.S. Cl. .................................... 351/206; 351/208; 354/62

[58] Field of Search .............. 351/205, 206, 207, 208, 351/211, 221; 354/62

[56] References Cited

U.S. PATENT DOCUMENTS 4,187,014  2/1980  Kato et al. ........................ 351/206
4,511,227  4/1985  Nurokawa et al. ................. 351/208

Primary Examiner—Rodney B. Bovernick
Assistant Examiner—P. M. Dzierzynski
Attorney, Agent, or Firm—Brumbaugh, Graves, Donohue & Raymond

[57] ABSTRACT

An eye fundus camera for taking photographs of a patient's eye fundus. The camera includes a pair of viewing targets located at the opposite sides of the optical axis. A switch is provided for alternately energizing the targets so that an appropriate one of the targets emits light beams when the camera housing is placed to take photographs of one of the patient's eyes.

4 Claims, 4 Drawing Sheets

EYE FUNDUS CAMERA HAVING VIEWING TARGETS

This application is a continuation of application Ser. No. 016,502, filed on Feb. 18, 1987, which, in turn, is a continuation application of Ser. No. 648,650, filed Sept. 7, 1984, both abandoned.

BACKGROUND OF THE INVENTION

The present invention relates to an eye fundus camera, and more particularly to an eye fundus camera having a viewing target for determining direction of viewing axis of a patient's eye.

PRIOR ART

In photographing the fundus or retina of a patient's eye by means of an eye fundus camera, it is required to determine the direction of viewing axis of the patient's eye in order that a desired area be appropriately photographed. For this purpose, an eye fundus camera is usually provided with a viewing target to have the patient's eye fixed on the target. For example, a conventional eye fundus camera has a small light source such as a lamp which is located outside the housing of the camera for movement in transverse directions. The operator of the camera is obliged to adjust the location of the lamp while watching the image of the fundus of the patient's eye. Further, when it is desired to take photographs of both eyes of the patient, the direction of the viewing axis of the patient's eye must be changed depending on which one of the left and right eyes is being photographed so that the viewing target must be moved frequently. It should further be noted that the aforementioned viewing target is located at a near point with respect to the patient's eye so that there may be a possibility that the pupil aperture will be reduced by putting the viewing point at the viewing target unless a pupil opening agent is used. Such reduced pupil aperture makes photographing difficult since the illumination light beam and the photographing light beams are both passed through the pupil aperture.

It is possible to locate optically the viewing target at a far point with respect to the patient's eye. For this purpose, proposals have been made to provide a viewing target projecting optical system in the housing of an eye fundus camera. It should however be noted that, even in this type of camera, the viewing target must be moved or selected depending on the eye to be photographed. Such procedures are very difficult to perform because the photographing by an eye fundus camera is carried out in a relatively dark room.

SUMMARY OF THE INVENTION

It is therefore an object of the present invention to provide an eye fundus camera which has a viewing target but is simple to handle.

Another object of the present invention s to provide an eye fundus camera having a viewing target, in which an appropriate viewing target is automatically selected depending on the patient's eye to be photographed.

SUMMARY OF THE INVENTION

The present invention is based on the recognition of the fact that the photographing field is substantially determined by a field angle and characterized by a pair of viewing targets, one for the left eye and the other for the right eye of the patient, the viewing target being automatically selected in response to a movement of the eye fundus camera from one position for photographing one of the eyes to the other position for photographing the other eye. Thus, according to the present invention, there is provided an eye fundus camera comprising housing means, objective lens means provided in said housing means and adapted to be placed opposite to a patient's eye, an illumination system provided in said housing means for projecting beams of illumination light through said objective lens means to said patient's eye, a photographing optical system provided in said housing means for photographing fundus of the patient's eye through said objective lens means, viewing target projecting system provided in said housing means for projecting an image of a viewing target through said objective lens means to said fundus of the patient's eye, means for displacing said housing means in a transverse direction with respect to the patient for photographing respective ones of the patient's eyes, said viewing target projecting system including a pair of viewing targets located opposite sides of optical axis of said objective lens means and means for passing light beams from one of said viewing targets selectively in response to a transverse position of the housing means.

According to the features of the present invention, an appropriate one of the viewing targets is automatically selected when the camera is displaced transversely from one position for photographing one of the patient's eyes to another position for photographing the other eye. Therefore, it is not required to adjust the location of the viewing target in each photographing operation.

DESCRIPTIONS OF THE PREFERRED EMBODIMENT

Figure 1:
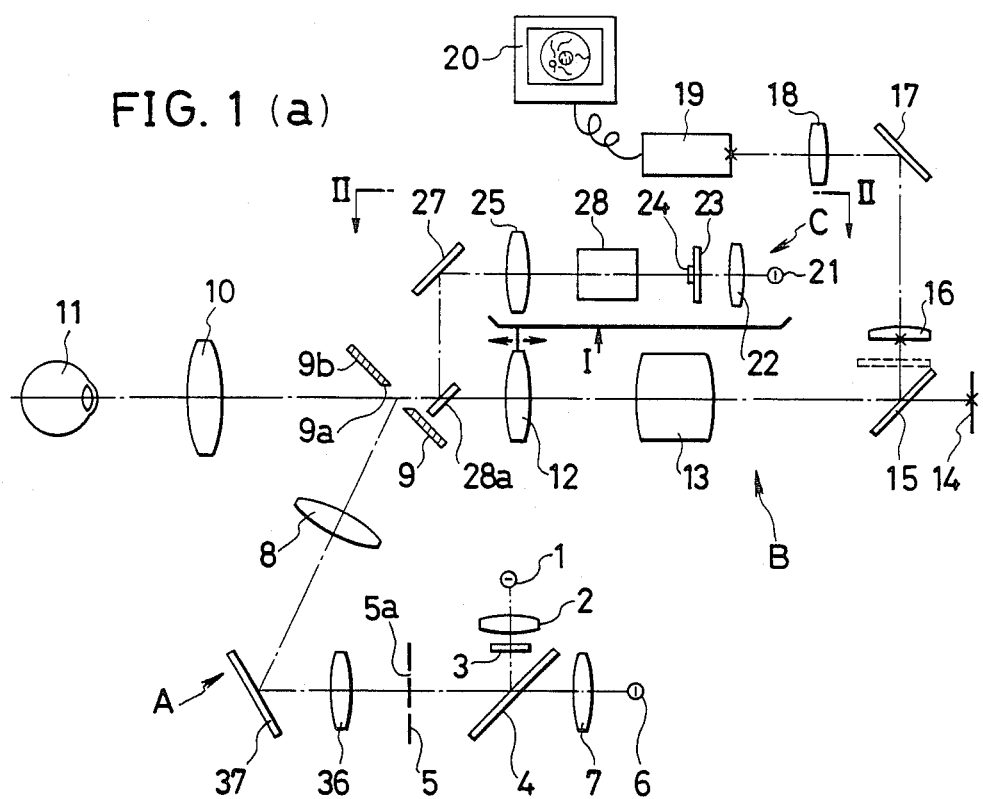
FIG. 1(a) is a diagrammatical illustration of the optical system of an eye fundus camera in accordance with one embodiment of the present invention.
FIG. 1(b) is a view as seen in the direction of arrows II—II in FIG. 1(a)
Figure 1:
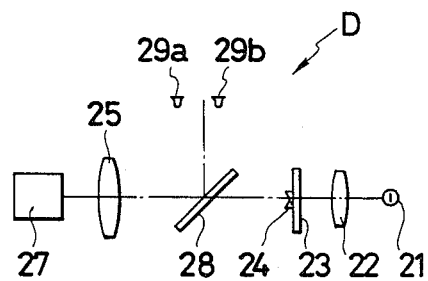

Referring to FIGS. 1(a) and (b), the optical system of the eye fundus camera shown therein includes an illumination optical system A for illuminating the fundus of a patient's eye, an observing and photographing optical system B for observing and photographing the patient's eye fundus, a focusing mark projecting system C for detecting focusing condition of the photographing optical system B and a viewing target projecting system D for projecting beams of light from the viewing target to the patient's eye fundus.

Illumination Optical System A

The illumination optical system A includes an observing light source 1 for producing beams of illuminating light which are passed through a condenser lens 2 and an infrared filter 3 to a slanted half mirror 4 and reflected thereby to a ring-aperture plate 5. The filter 3 functions to block visual rays and allows infrared rays to pass therethrough. The system further has a photographing light source 6. Beams of light from the light source 6 are passed through a condenser lens 7 and the half-mirror 4 to the aperture plate 5. The aperture plate 5 has a ring-shaped aperture 5a and the beams of light which have passed through the aperture 5a in the plate 5 are passed through a relay lens 36 to a slanted mirror 37 which reflects the light beams to a relay lens 8. The light beams are then passed through the relay lens 8 to a slanted apertured mirror 9 which has a central aperture 9a and a peripheral reflecting surface 9b. The light beams are reflected by the reflecting surface 9b of the mirror 9 toward an objective lens 10 which is adapted to be placed opposite to a patient's eye 11 with a working eye. The light beams are thus projected through the objective lens 10 to the fundus of the patient's eye 11.

Observing and Photographing Optical System B

The light beams are reflected at the fundus of the patient's eye 11 and passed through the objective lens 10 along the optical axis thereof. Along the optical axis, there are provided a focusing lens 12 and an imaging lens 13 and the light beams which have passed through the central aperture 9a of the mirror 9 are focused by these lenses 12 and 13 on photographing film plane 14 to produce an image of the fundus of the patient's eye 11. In front of the film plane 14, there is provided a retractable mirror 15 which is inserted into the optical path for observation as shown by solid lines in FIG. 1(a) but retracted to the position as shown by dotted lines for photographing. It will therefore be understood that, for observation, the light beams which have passed through the imaging lens 13 are reflected by the mirror 15 to be focused on a field lens 16 which is conjugate with the film plane 14. The image produced on the field lens 16 is relayed through a mirror 17 and a relay lens 18 to an photoelectric surface of an image taking tube 19. The image pick-up tube 19 produces electric signals in accordance with the image produced thereon. The signals are applied to a monitor TV 20 for displaying an visual image of the eye fundus.

Focusing Mark Projecting System C

Figure 2:
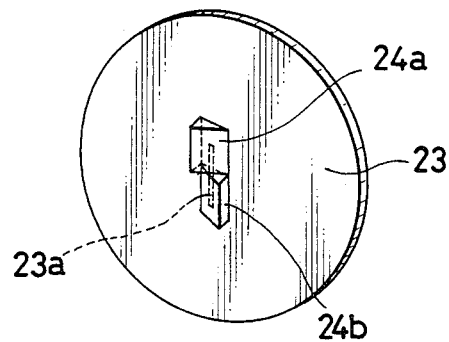
FIG. 2 is a perspective view showing a focusing mark plate.

The focusing mark projecting system C includes a slit mark plate 23 which includes a slit 23a as shown in FIG. 2. On the slit mark plate 23, there is provided a deflecting prism assembly 24 comprising deflecting prisms 24a and 24b. The system C further includes a light source 21 which produces beams of light or infrared wavelengths. The light beams from the light source 21 are passed through a condenser lens 22 to the mark plate 23 and the light-beams which have passed through the mark slit 23a are divided into two fluxes by means of the deflecting prisms 24a and 24b. The light fluxes are then passed through a relay lens to a slanted mirror 27 which reflects the light fluxes toward a mirror 28a. The mirror 28a has two reflecting areas which reflect the two fluxes separately toward the mirror 9. The light fluxes reflected at the mirror 28a are then passed through the central aperture 9a of the mirror 9 and the objective lens 10 to the patient's eye fundus to form a slit image. The slit image formed on the eye fundus is observed by the monitor TV 20 together with the image of the eye fundus. The light source 21, the condenser lens 22, the slit mark plate 23 and the deflecting prism assembly 24 are movable as a unit with the focusing lens 12 of the optical system B along the optical axis so that the focusing of the optical system can be performed by moving these elements to a position wherein a single image of the mark slit 23a is formed.

Viewing Target Projecting System D

The system D includes a slanted wavelength selecting mirror 28 which is located between the slit mark plate 23 and relay lens 25. The mirror 28 functions to allow the infrared rays to pass therethrough but to reflect visual rays. A pair of viewing target 29a and 29b are provided symmetrically with respect to a reflecting optical axis of the mirror 28. The viewing target 29a and 29b are provided by light emitting diodes producing green lights and conjugate with the mark slit 23a in the plate 23. The light beams from the targets 29a and 29b are reflected by the mirror 28 and passed through the optical path which has been described with reference to the focusing mark projecting system C.

The viewing targets 29a and 29b are respectively for left and right eyes of the patient. As will be described later in detail, when the eye fundus camera is shifted for photographing the left eye, the target 29a is energized whereas the target 29b is energized when the eye fundus camera is shifted for photographing the right eye. By having the patient's eye view the target which is being energized, it is possible to determine the direction of sight of the patient's eye to thereby take photographs of an appropriate area of the eye fundus. The targets 29a and 29b are conjugate with the focusing mark slit 23a so that the image of the target can be focused on the eye fundus when the eye fundus image is focused. It should further be noted that the patient can observe the target at a far point so that there will be not problem of the patient's pupil aperture being reduced.

Structure of the Eye Fundus Camera

Figure 3:
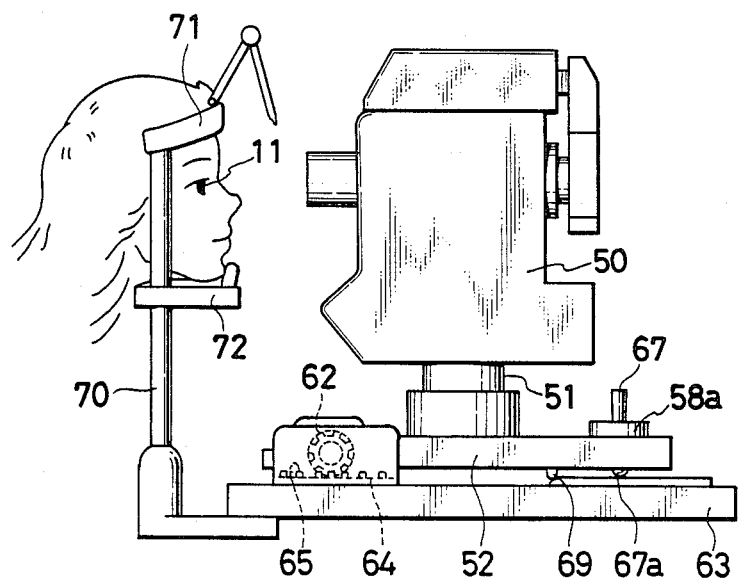
FIG. 3 is a side elevational view of the eye fundus camera.
Figure 4:
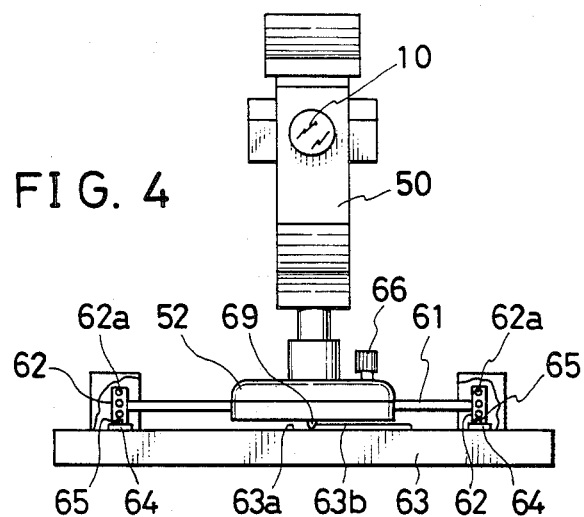
FIG. 4 is a front elevational view of the eye fundus camera.
Figure 5:
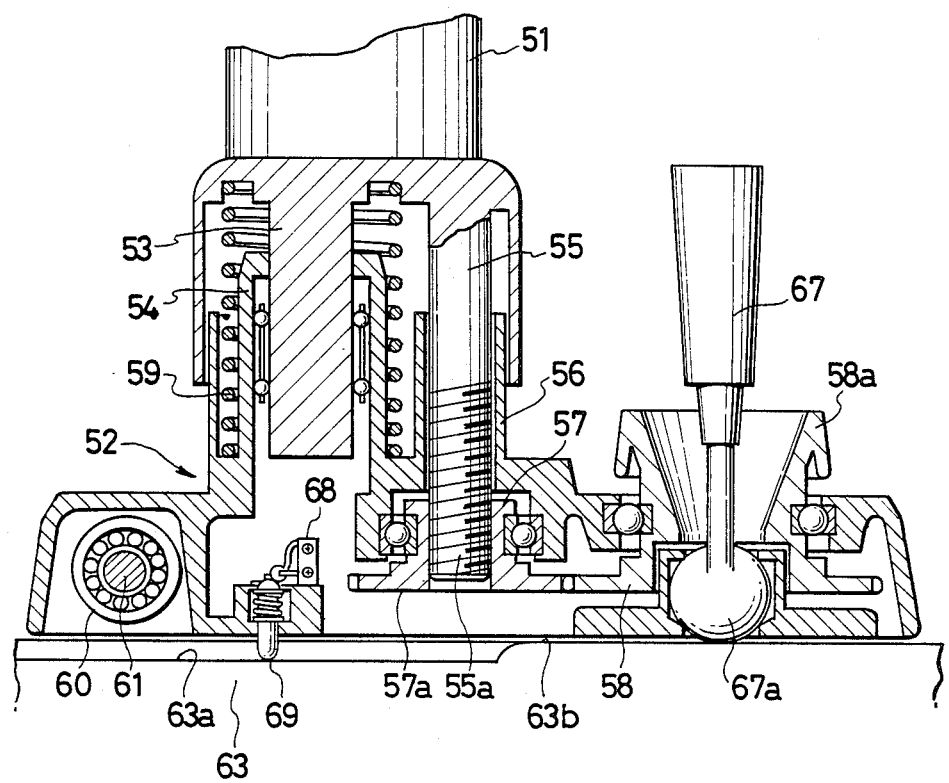
FIG. 5 is a sectional view of the eye fundus camera specifically showing the transverse displacing mechanism adopted therein.
Figure 6:
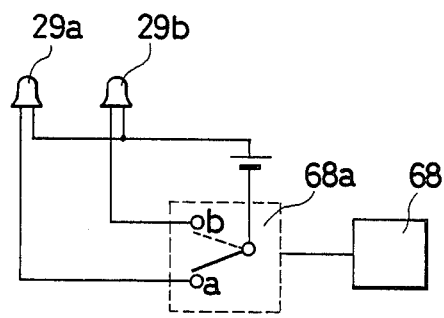
FIG. 6 is a diagram showing the switching circuit for the viewing targets.

Referring to FIGS. 3 and 4 and 5, there is shown an eye fundus camera having a housing 50 in which the aforementioned optical system is arranged. The housing 50 has a post 51 which is extending downward from the housing 50 and carried at the bottom end by a carriage 52. In order to make it possible to adjust the height of the housing 50, the post 51 is provided with a downwardly extending guide rod 53 and the carriage 52 is provided with a guide tube 54 for receiving and vertically guiding the rod 53. The post 51 is further formed with a downwardly extending screw rod 55 which extend through a guide tube 56 provided in the carriage 52. The screw rod 55 is formed at the lower portion with external threads 55a which are engaged with internal thread in a nut 57 which is mounted rotatably on the carriage 52.

The nut 57 is integrally formed with an external gear 57a which is in meshing engagement with an external gear 58 mounted rotatably on the carriage 52. The external gear 58 is integrally formed with an operating knob 58a which projects upward through the carriage 52. With this arrangement, it is possible to move the post 51 and therefore the housing 50 in vertical directions. Around the guide tube 54, there is disposed a coil spring 59 which acts between the lower end of the post 51 and the carriage 52 to support the weight of the eye fundus camera.

The carriage 52 is provided at the front portion with a bearing 60 which receives a transverse guide rod 61 for rotation and axial sliding movement. As shown in FIG. 4, the guide rod 61 is provided at the opposite ends with wheels 62 which rotate along tracks 64 formed on a table 63. On the track 64, there are a plurality of pins 64 which are located at regular spacings and the wheel 62 is formed with holes 62a for receiving the pins 65. Thus, the wheel 62 is guided along the track 64 through the engagement between the hole 62a in the wheel 62 and the pin 65. The guide rod 61 is axially slidable with respect to the bearing 60 so that the carriage 52 is displaceable transversely along the guide rod 61. In order to fix the carriage 52 on the guide rod 61, there is provided a locking mechanism (not shown) which is actuated by an operating knob 66 shown in FIG. 4.

At the right side with respect to the objective lens 10 in FIG. 4, the table 63 is formed with a raised flat portion 63b which is raised from a flat surface 63a as clearly shown in FIG. 5. At the rear end portion of the carriage 52, there is rotatably supported a spherical portion 67a of an adjusting stick 67. The spherical portion 67a is in contact with the upper surface of the table 63 so that an actuation of the stick 67 causes a shifting movement of the carriage 52. The carriage 52 is provided with a microswitch 68 and a switch actuating pin 69 which extends downward from the carriage 52. At the front end portion, the table 63 is provided with a support 70 which carries a forehead rest 71 and a chin rest 72 so that the patient is held with its eye 11 opposite to the objective lens 10.

Operation

In the structure described above, when the stick 67 is actuated to move the housing 50 rightward as seen in FIG. 4 to have the objective lens 10 be located opposite to the right eye of the patient, the switch actuating pin 69 rides on the raised flat portion 63b so that the switch 68 is actuated. The signal from the switch 68 is passed to a selection switch 68a to turn a switch arm from a normal terminal b to another terminal a so that the target 29a is energized. To photograph the left eye, the target 29b is energized. It will thus be understood that a simple transverse displacement of the camera housing 50 for aligning the objective lens 10 to either one of the patient's eyes energizes an appropriate one of the targets 29a and 29b.

Figure 7A:
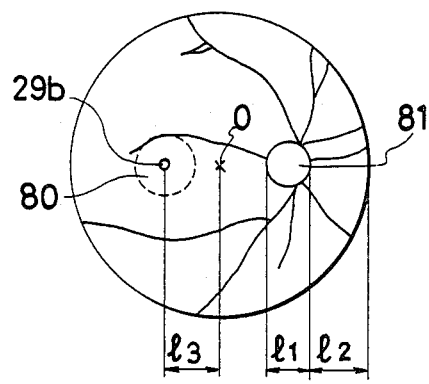
FIGS. 7(a) and (b) show images of left and right eyes, respectively.
Figure 7B:
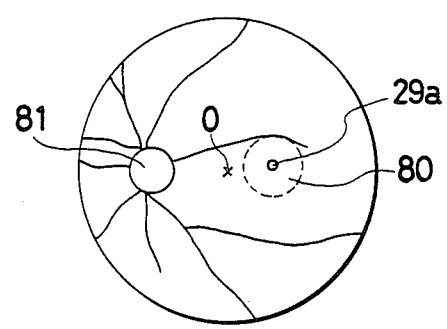

FIG. 7(a) shows an image of an eye fundus when the target 29b is energized for photographing the right eye in an eye fundus camera having a field angle of 45°. When the patient looks at the target 29b, the image of the target 29b is formed at the yellow spot 80 on the eye fundus. It is therefore possible to take photographs of the field as shown. Where the field angle is 45°, it is general to have a photographing field $l_2$ at the nose side from the disk 81 1.5 times as large as the diameter $l_1$ of the disk 81. Based on this fact, the target 29b is offset from the optical axis 0 by a distance corresponding to the distance $l_3$ shown in FIG. 7(a). FIG. 7(b) shows an image of the left eye fundus with the target 29a energized. It should of course be noted that the targets may not necessarily be fixed but may be made adjustable. Further, the targets may be blinked to draw the patient's attention thereon.

The invention has thus been shown and described with reference to a specific embodiment, however, it should be noted that the invention is in no way limited to the details of the illustrated structures but changes and modifications may be made without departing from the scope of the appended claims.

I claim:

1. An eye fundus camera comprising housing means, objective lens means provided in said housing means and adapted to be placed opposite to a patient's eye, an illumination system provided in said housing means for projecting beams of illumination light through said objective lens means to said patient's eye, a photographing optical system provided in said housing for photographing the fundus of the patient's eye through said objective lens means, viewing target projecting system provided in said housing means for projecting an image of said viewing target through said objective lens means to said fundus of the patient's eye so as to determine the direction of the viewing axis of the patient's eye, means for displacing said housing means in a transverse direction with respect to the patient for photographing respective ones of the patient's eyes, said viewing target projecting system including a pair of viewing targets located at opposite sides of and offset from the optical axis of said objective lens means, a first one of said viewing targets being energized when a left eye of the patient is photographed and a second one of said viewing targets being energized when a right eye of the patient is photographed, said targets being selectively automatically energized in response to said transverse displacement of the housing means, and light passing means for passing light beams from one of said viewing targets automatically and selectively in response to a transverse position of the housing means so that a desired photographing field is obtained when the patient's eye looks at the target.

2. An eye fundus camera in accordance with claim 1 in which said targets are fixed in position relative to the housing.

3. An eye fundus camera in accordance with claim 1 in which said viewing targets are light emitting elements which emit light beams when energized, the light beam passing means being switching means for alternately energizing the viewing targets.

4. An eye fundus camera in accordance with claim 3 in which said housing means is mounted on table means for displacement in a horizontal plane, said table means having a raised portion at one side for actuating said switching means when said housing means is displaced to said one side for having one of the patient's eyes aligned to said objective lens means.

* * * * *